United States Patent
Reynaud et al.

(10) Patent No.: US 10,524,887 B2
(45) Date of Patent: Jan. 7, 2020

(54) CAD/CAM-MACHINABLE DISC FOR THE MANUFACTURE OF FIBER INLAY-CORES

(71) Applicant: SOCIETE DE RECHERCHES TECHNIQUES DENTAIRES—RTD, Saint Egreve (FR)

(72) Inventors: Pierre-Luc Reynaud, Vaulnaveys le Haut (FR); Manh-Quynh Chu, Fontanil Cornillon (FR); Mélissa Gonzalez, Saint Martin d'Heres (FR); Cyril Rajon, Quaix en Chartreuse (FR)

(73) Assignee: SOCIETE DE RECHERCHES TECHNIQUES DENTAIRES—RTD, Saint Egreve (FR)

( * ) Notice: Subject to any disclaimer, the term of this patent is extended or adjusted under 35 U.S.C. 154(b) by 0 days.

(21) Appl. No.: 16/061,217

(22) PCT Filed: Oct. 17, 2016

(86) PCT No.: PCT/FR2016/052677
§ 371 (c)(1),
(2) Date: Jun. 11, 2018

(87) PCT Pub. No.: WO2017/098096
PCT Pub. Date: Jun. 15, 2017

(65) Prior Publication Data
US 2018/0360575 A1 Dec. 20, 2018

(30) Foreign Application Priority Data

Dec. 10, 2015 (FR) ..................... 15 62143

(51) Int. Cl.
*A61C 13/00* (2006.01)
*A61C 5/70* (2017.01)
(Continued)

(52) U.S. Cl.
CPC ............ *A61C 13/0004* (2013.01); *A61C 5/73* (2017.02); *A61C 5/77* (2017.02); *A61C 8/0016* (2013.01);
(Continued)

(58) Field of Classification Search
CPC ... A61C 13/0022; A61C 13/0004; A61C 5/73; A61C 8/0016; A61C 8/00; A61C 8/0037;
(Continued)

(56) References Cited

U.S. PATENT DOCUMENTS 6,334,775 B2 * 1/2002 Xu ........................... A61C 5/00
433/228.1
2002/0086266 A1 7/2002 Karmaker et al.
(Continued)

FOREIGN PATENT DOCUMENTS

EP 0040165 11/1981
EP 0432001 6/1991
(Continued)

OTHER PUBLICATIONS

International Search Report (English) and Written Opinion dated Jan. 17, 2017, from International Application No. PCT/FR2016/052677, 14 pages.

*Primary Examiner* — Joanna Pleszczynska
(74) *Attorney, Agent, or Firm* — Meunier Carlin & Curfman LLC

(57) ABSTRACT

The invention concerns a preform for a CAD/CAM machining apparatus having an upper face and a lower face a11d in which at least one of the cells is filled with a composite material to be machined by CAD/CAM, said material comprising long unidirectional fibers embedded in a cross-linked polymer matrix.

15 Claims, 1 Drawing Sheet

(51) Int. Cl.

| | | |
|---|---|---|
| *A61C 5/73* | (2017.01) | |
| *A61C 5/77* | (2017.01) | |
| *C08J 5/24* | (2006.01) | |
| *A61C 8/00* | (2006.01) | |
| *C08J 3/24* | (2006.01) | |
| *B29C 39/10* | (2006.01) | |
| *B29K 105/10* | (2006.01) | |
| *B29K 33/04* | (2006.01) | |
| *B29K 105/20* | (2006.01) | |
| *B29K 105/24* | (2006.01) | |
| *B29K 663/00* | (2006.01) | |

(52) U.S. Cl.
CPC ............. *A61C 13/0022* (2013.01); *C08J 3/24* (2013.01); *C08J 5/24* (2013.01); *B29C 39/10* (2013.01); *B29K 2033/04* (2013.01); *B29K 2105/107* (2013.01); *B29K 2105/20* (2013.01); *B29K 2105/24* (2013.01); *B29K 2663/00* (2013.01); *C08J 2331/02* (2013.01); *C08J 2333/10* (2013.01); *C08J 2333/12* (2013.01); *C08J 2333/14* (2013.01); *C08J 2335/02* (2013.01); *C08J 2363/00* (2013.01); *C08J 2369/00* (2013.01); *C08J 2371/02* (2013.01); *C08J 2375/04* (2013.01)

(58) Field of Classification Search
CPC ... A61C 13/00; A61C 5/77; Y10T 428/24124; Y10T 428/24132; Y10T 428/24174; C08J 5/24

See application file for complete search history.

(56) References Cited

U.S. PATENT DOCUMENTS

| | | | |
|---|---|---|---|
| 2003/0176126 | A1 | 9/2003 | Mulligan et al. |
| 2004/0241614 | A1* | 12/2004 | Goldberg ............ A61C 13/0003 433/202.1 |
| 2009/0130634 | A1 | 5/2009 | Ganley et al. |
| 2009/0258965 | A1* | 10/2009 | Lassila ................ A61K 6/0023 523/116 |
| 2015/0125822 | A1* | 5/2015 | Cramer Von Clausbruch ............ A61C 13/0022 433/202.1 |

FOREIGN PATENT DOCUMENTS

| | | |
|---|---|---|
| FR | 2588181 | 4/1987 |
| WO | 2009144901 | 12/2009 |
| WO | 2009154301 | 12/2009 |
| WO | 2010109496 | 9/2010 |

\* cited by examiner

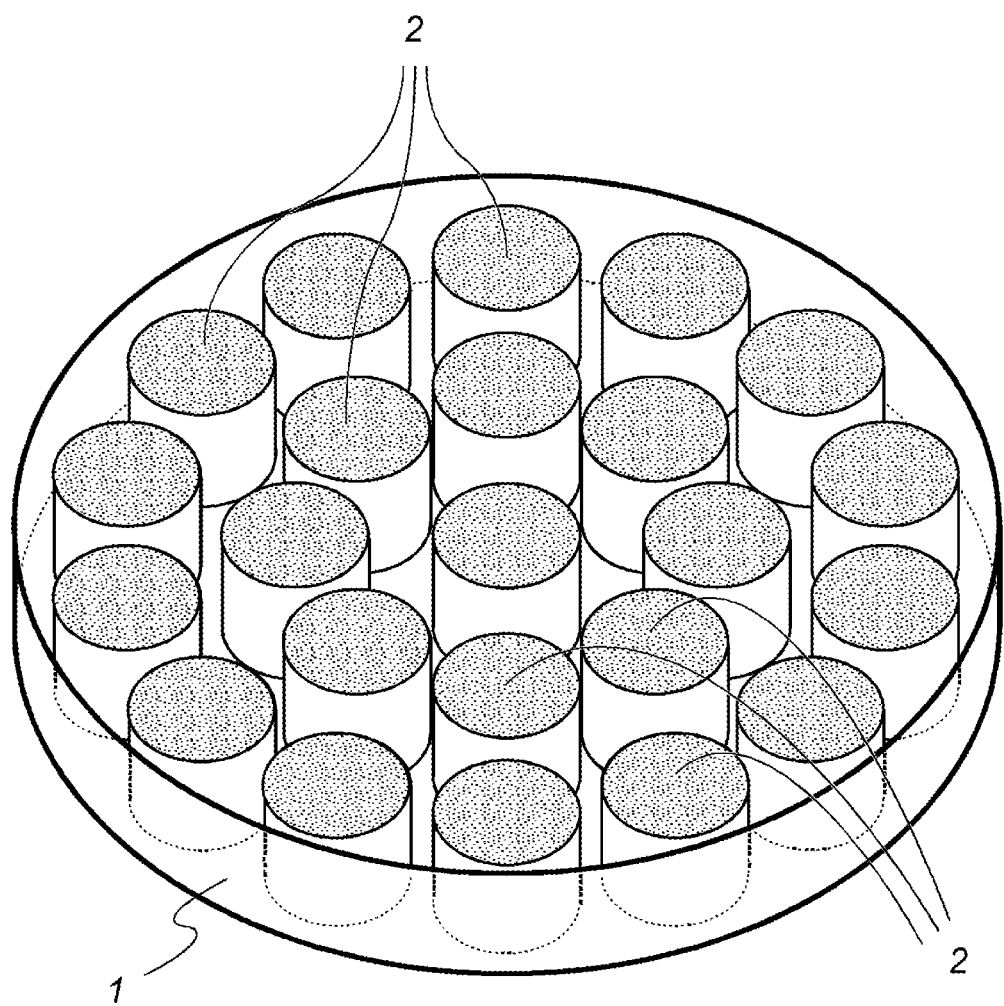

CAD/CAM-MACHINABLE DISC FOR THE MANUFACTURE OF FIBER INLAY-CORES

The object of the invention is a preform or support, preferably a standardized disc for CAD/CAM machining apparatuses or more generally, a CAD/CAM machining support for the manufacture of fiber inlay cores (tenon and core restoration), notably tenons and implant (abutment) screws. It also concerns a process for the manufacture of said support. An additional object is the inlay cores, bolts and implant screws obtained by the CAD/CAM.

The invention will hereafter be described in relation to inlay cores.

The inlay core is a monobloc piece formed of a tenon mounted on an abutment. It is made of metal, more rarely of ceramic. It is a single piece, which is why it is designated "monobloc" (core). It is therefore formed of the same material. The inlay core serves to support the external reconstitution of a tooth, specifically a crown.

The metal alloys used to manufacture the inlay cores are typically stainless steel and sometimes semi-precious metals. Their primary disadvantage is that they are subject to chemical or electrochemical erosion. They also have a modulus of elasticity greater than that of dentin which can, over time, cause deterioration of the inlay core. It is difficult, then, to re-access the root canal to remove the inlay core in the event of an apical infection.

In manufacturing, the inlay core can be obtained by machining the preforms of metal alloy or ceramic via CAD/CAM. It can also be obtained by lost-wax casting in the dental laboratory.

To overcome the drawbacks found in using metals, the applicant has developed tenons using a composite fiber around which the practitioner can form the core reconstitution using a polymer resin. The core must be glued to the tenon, creating an additional interface that the practitioner must master to perfection. The core reconstitution, then, fills the empty space left by the tooth and serves to support the actual crown. This type of structure is a substitute for the inlay core and, apart from the type of material, the difference is that it is manufactured in 2 pieces instead of one piece.

The tenons made of composite fibers are described in documents FR-A-2588181 and EP-A-432 001. Said tenons form long unidirectional fibers, of glass or carbon, more generally of any material having elevated mechanical characteristics. Said fibers represent from 60 to 70% of the tenon by volume. The fibers are cleaned by pultrusion in a matrix of biocompatible thermosetting resin, notably epoxy or polyepoxy, polyester, vinylester, acrylic or methacrylic resins.

Pultrusion is used to form rods between 2 and 5 mm in diameter. Once cross-linked and re-cooled, the rods are machined to the desired form.

Next, the practitioner adjusts the tenon to the length desired and fills the gap left by the tooth with a composite paste.

No solution has been offered for the manufacture of a monobloc composite fiber inlay core, that is, the inlay core made of unidirectional fibers embedded in a polymer matrix. The use of CAD\CAM would be ideal, but no technique has yet been perfected.

Machining dental protheses, specifically crowns and bridges, using CAD/CAM (Computer Assisted Design/Computer Assisted Manufacturing) is well known. This technology has been described in document EP040165B1. The technology has evolved since then, both in the CAD/CAM material and the composition of preforms. Document WO2010/109496 describes a preform of a composite material formed by superimposing parallel fibrous webs imbedded in a polymer matrix. The webs are divided over the entire thickness of the preform and are each re-bonded by transversal filaments. The preform is used to make the crowns. According to one essential characteristic, the webs are spun in specific patterns, the weft filaments going in a different direction from the warp filaments. Said preform is problematic as it cannot be used for machining the inlay core because the mechanical resistance of the composite material is not sufficient.

Document US2002/086266 A1 describes a preform of a composite material that can potentially be machined using CAD/CAM. It is used in the manufacture of crowns, bridges, tenons, inlays, etc. This document makes no reference to inlay cores. To manufacture tenons, the preform is in the form of a rod, the diameter of which is chosen to correspond to that of the root canal. Under these conditions, the current CAD/CAM is not suitable for preforms, which are sized to receive preforms in disc form with a standard diameter of 98 mm.

Document US2003/0176126 describes a fibrous monolithic material consisting of extruded filaments. The filaments are in a core/sheath structure obtained by extruding a mixture of powders containing polymer binders. The filaments are then bound to each other in various ways, even weaving, to form bundles. The composite material obtained is then applied to the surface of the material to improve hardness.

The problem designed to be resolved by the invention is to offer a preform that can be machined by CAD/CAM to manufacture core inlay composite fibers, tenons, or implant screws.

One solution would be to manufacture a preform in the form of a fibrous composite rod with a diameter of 98 mm. This is not a solution because it is not economically viable. In fact, to make rods containing from 60 to 70% fibers by volume, the number of fiber coils needed to obtain a diameter of 98 mm would be too great—about 10,820 weft fibers!

The applicant had the idea of incorporating portions of the unidirectional fibrous rods embedded in a polymer matrix into adapted cells arranged on a support.

More precisely, the object of the invention is a support or preform for a CAD/CAM machining tool with an upper face and a lower face containing at least one cell filled with a composite material to be machined using CAD/CAM, said material containing long unidirectional (UD) fibers embedded in a cross-linked polymer matrix.

In practice, the composite material contains at least 80%, preferably at least 90%, more preferably 100% long UD fibers, that is, fibers parallel to each other.

In a preferred method of construction, the composite contains at least 80%, preferably at least 90%, more preferably 100% long UD fibers positioned vertically in the matrix in relation to upper and lower surfaces of the support.

Further in the description and in the claims, the words "preform" and "support" are used interchangeably to designate the object of the invention.

In other words, the invention consists of manufacturing rods, notably by pultrusion, preferably circular, formed of UD fiber rods in a polymer matrix. The rods are then cut into several pieces and positioned in the circular cells of a support. In practice, the support is in the form of a disc with dimensions corresponding to those of a standard CAD/CAM disc. In practice, this is a disc 98 mm in diameter. It is thus suitable for current machines.

In a particular embodiment, the preform contains only one cell. Under those conditions, the preform is a parallelepiped shape 14×14 square and 18 mm long.

It is thus possible to manufacture fiber composite inlay cores using CAD/CAM from an adapted preform.

Further in the description, the expression "portion or rod section" is used to indicate composite fiber material filling the cells. This material will be machined for the inlay cores, tenons or implant screws.

The invention also concerns the inlay core composite fibers comprising long longitudinal unidirectional fibers (UD) embedded in a cross-linked polymer matrix. CAD/CAM may be used to machine said inlay cores. To the applicant's knowledge, the inlay cores obtained using CAD/CAM for a preform made of the composite material as described above has never been proposed. The same is true of tenons and implant screws.

Of course, the support can be in a form other than cylindrical based on the CAD/CAM apparatus used and their evolution. Similarly, the sections can be square, rectangular and generally any geometric form based on the section used. The cell dimensions will of course also be based on the rod and the product to be machined: inlay core, tenon or screw. The cell diameter is 3 to 18 mm, preferably 20 mm with a depth advantageously between 10 and 24 mm, preferably about 16 mm.

The rods will generally fill 100% of the volume of each cell.

Advantageously, the cells abut each face of the support such that the composite material gravitates toward each of the faces. Said characteristic, combined with the fact that the entire volume of the cells is filled with composite material, allows for a symmetrical support than can be used for any purpose, facilitating the work of the practitioner.

The cells can of course also be separated and fit with a bottom. Under these conditions, the support can be used only in the direction that accesses the machining tool. The latter will or will not access the composite material, depending on the thickness of the support covering the cells.

The support as such can be hollow. In that case, the cells have a lateral wall linking the upper and lower faces of the support. This is preferably fabricated from plastic.

Advantageously, the support is full, that is, it is made of thermoplastic or thermosetting resin over the entire thickness and between each cell.

According to an essential characteristic, the rods must be held in a fixed position in the cells. Once machining starts, they cannot move or it would change the form of the inlay core, tenon or screw programmed by the software.

Any method can be used to secure the support for the portions or rod sections.

In a first embodiment, they can be inserted forcibly into cells with a slightly somewhat smaller diameter.

In another embodiment, the rod sections are glued to all or part of the cell wall with an adhesive layer. This is done when the resin forming the matrix and that forming the support are not identical or not compatible.

In a preferred embodiment, the plastic forming the support when fabricated is advantageously poured around the rod sections within an adapted mold. To fix the rods into the cells, the materials forming the matrix into which the fibers and support are embedded are identical or compatible. They are chosen by the one skilled in the art based on the properties desired.

In all cases, it is a resin chosen from among a group of thermosetting resins containing PMMA, TEGDMA, BIS-GMA, BDMA, HDDMA, UDMA, epoxy and vinylester, or a group of thermosetting resins, notably PC, POM, PU.

The fibers are chosen from the group of glass fibers such as E, R, S, AR and XRO fibers, particularly silica (quartz).

Advantageously, the proportion of the long fibers is 40 to 80%, preferably 60 to 70% by volume of the polymer matrix, with the matrix bringing it to 100%.

As previously stated, the support is first and foremost used to fabricate the inlay core. However, it can also be used to fabricate tenons or implant screws. All these structures show all the characteristics previously described regarding the type of fibers, the matrix, and fiber volume.

The subject of the invention is also a method for manufacturing a support as described above.

This process includes the following steps in forming a mold:
   the cylinders or rod sections forming the long longitudinal unidirectional fibers embedded in a cross-linked polymer matrix are positioned,
   a resin is poured between each cylinder,
   said resin is cross-linked,
   the support formed by the cross-linked resin containing the rod sections is unmolded.

As previously stated, the support resin is advantageously chosen to allow the rods to be set without adding an adhesive.

Preferably, the mold is circular, approximately 98 mm in diameter and between 10 and 24 mm thick, preferably about 16 mm.

The invention also concerns the use of the support previously described for the manufacture of the inlay core, tenons, or implant screws machined by CAD/CAM from the composite material filling the cells.

The invention and resulting benefits will become clear from the following examples supported by the attached FIGURES.

FIG. 1 is a perspective view of the support according to the invention.

A rod comprising 81% by weight (64% volume) of unidirectional glass fibers AR and 19% of epoxy resin matrix is manufactured by pultrusion. The rod diameter is 12 mm. The rods are cut into 16 mm sections.

Thirty 12 mm rod sections or nineteen 14 mm portions as marked are positioned in a mold that is 98 mm in diameter and 16 mm thick.

Then an acrylic resin cold-polymerized with a peroxide-based catalyst is poured into the mold.

Lastly, the support is unmolded. This includes the cells filled by the rod sections. The CAD/CAM then inserts a disc into a machining apparatus. To facilitate indexing in the CAD/CAM machine, each portion of the rod is marked. The CAD/CAM then machines each portion to obtain the inlay cores, tenons, or even implant screws. These structures are made of composite fibers wherein the fibers are longitudinal and unidirectional.

The support thus obtained is shown is FIG. 1. It constitutes the support itself (1) shown in disc form with each of its 23 cells filled with a rod section (2). Each portion of the rod is machined by the CAD/CAM. Depending on the diameter of the rods, the disc can contain more cells.

The invention and its advantages will be seen clearly in the following example. This is shown as a non-limiting example for the one skilled in the art. It is thereby shown that inlay cores of composite fibers can be manufactured using CAD/CAM.

The invention claimed is:

1. A preform for a CAD/CAM machining apparatus, the preform having an upper face and a lower face and comprising at least one cell filled with a composite material to be machined by CAD/CAM, said composite material comprising fibers embedded in a cross-linked polymer matrix, wherein at least 80% of the fibers are longitudinally oriented unidirectional fibers that are vertical to the upper and lower faces of the preform, wherein a material in the preform surrounding the at least one cell includes a resin and does not include fibers.

2. The preform according to claim 1, wherein the at least one cell abuts each of the upper and lower faces of the preform and an entire volume of the cell is filled with the composite material.

3. The preform according to claim 1, wherein the at least one cell is cylindrical.

4. The preform according to claim 3, wherein the at least one cell is 3 to 20 mm in diameter.

5. The preform according to claim 1, wherein the preform is in disc form.

6. The preform according to claim 1, wherein material constituting the polymer matrix and the material surrounding the at least one cell are identical or compatible and are chosen from the group of thermosetting resins including PMMA, TEGDMA, BISGMA, BDMA, HDDMA, UDMA, epoxy and vinylester, or from the group of thermoplastic resins including PC, POM, and PU.

7. The preform according to claim 1, wherein the fibers are chosen from the group comprising glass fibers E, R, S, AR, and XRO, and silica.

8. The preform according to claim 1, wherein the fibers represent 40 to 80% by volume of the polymer matrix.

9. The preform according to claim 1, wherein at least 90% of the fibers are longitudinally oriented unidirectional fibers.

10. The preform according to claim 1, wherein 100% of the fibers are longitudinally oriented unidirectional fibers.

11. The preform according to claim 5, wherein the preform has a diameter of 98 mm.

12. The preform according to claim 8, wherein the fibers represent 60 to 70% by volume of the composite material.

13. The preform according to claim 4, wherein the at least one cell is 10 to 24 mm deep.

14. A process of fabricating the preform of claim 1,
positioning into the preform a plurality of cylinders, each cylinder constituted of long comprising the composite material comprising the longitudinal unidirectional fibers embedded in the cross-linked polymer matrix,
pouring the resin between each cylinder,
cross-linking said resin,
unmolding the preform formed from the cross-linked resin, including the cylinders.

15. A method of producing an inlay core, tenons, or implant screws comprising machining by CAD/CAM the composite material filling the at least one cell in the preform of claim 1.

* * * * *